(12) United States Patent
Ito et al.

(10) Patent No.: US 8,758,724 B2
(45) Date of Patent: Jun. 24, 2014

(54) UNNATURAL AMINO ACID RADIOLABELING PRECURSOR

(75) Inventors: Osamu Ito, Sodegaura (JP); Akio Hayashi, Sodegaura (JP); Fumie Kurosaki, Sodegaura (JP); Masahito Toyama, Sodegaura (JP); Toshiyuki Shinmura, Sodegaura (JP); Arinori Harano, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 798 days.

(21) Appl. No.: 12/085,679

(22) PCT Filed: Nov. 28, 2006

(86) PCT No.: PCT/JP2006/323659
§ 371 (c)(1),
(2), (4) Date: May 29, 2008

(87) PCT Pub. No.: WO2007/063824
PCT Pub. Date: Jun. 7, 2007

(65) Prior Publication Data
US 2008/0281121 A1    Nov. 13, 2008

(51) Int. Cl.
*A61K 51/00* (2006.01)
*A61M 36/14* (2006.01)

(52) U.S. Cl.
USPC ......................................... 424/1.65; 560/123

(58) Field of Classification Search
None
See application file for complete search history.

(56) References Cited

U.S. PATENT DOCUMENTS

| | | | |
|---|---|---|---|
| 5,360,928 A * | 11/1994 | Carpino et al. ............... | 562/849 |
| 5,808,146 A | 9/1998 | Goodman et al. | |
| 5,817,776 A | 10/1998 | Goodman et al. | |
| 7,071,191 B2 | 7/2006 | Apodaca et al. | |
| 7,910,745 B2 * | 3/2011 | Toyama et al. ............... | 548/123 |
| 2006/0039855 A1* | 2/2006 | Gibson et al. ................ | 424/1.11 |
| 2006/0292073 A1* | 12/2006 | Goodman et al. ............ | 424/1.11 |
| 2008/0139481 A1* | 6/2008 | Dix ................................ | 514/17 |

FOREIGN PATENT DOCUMENTS

| | | | |
|---|---|---|---|
| CA | | 2455598 A1 | 2/2003 |
| GB | WO | 2004056725 A1 | 7/2004 |
| JP | | 2000500442 T | 1/2000 |
| JP | | 2004-511438 A | 4/2004 |
| JP | | 2005-519861 A | 7/2005 |
| JP | | 2007-500730 A | 1/2007 |
| JP | | 2008-546783 A | 12/2008 |
| WO | | 97/17092 A1 | 5/1997 |
| WO | WO | 9960018 A1 * | 11/1999 |
| WO | | 03/011345 A1 | 2/2003 |
| WO | WO | 2004/056725 | 7/2004 |
| WO | WO-2004/056725 A1 | | 7/2004 |
| WO | | 2005/048810 A2 | 6/2005 |
| WO | | 2007/001958 A2 | 1/2007 |

OTHER PUBLICATIONS

Wang et al. Hateroatom Chemistry 2002, 77-83.*
Shoup et al. J. Labelled Cpd Radiopharm. 1999, 215-225.*
Martarello et al. J Med Chem, 2002, 45, 2250-2259.*
Gatley et al. Int. J. Appl. Rad. Isot. 1981, 32, 211-214.*
Allan et al. J. Med. Chem. 1990, 33, 2905-2915.*
Office Action, dated Dec. 22, 2010, in corresponding Chinese Application 200680044818.7 (English translation).
McConathy, J. et al., "Improved synthesis of anti-[18F]FACBC: improved preparation of labeling precursor and automated radiosynthesis", Applied Radiation and Isotopes 58 (2003) pp. 657-666.
Examination Report issued on Feb. 17, 2010 in New Zealand Application No. 568179.
Martarello, "Synthesis of syn- and anti-1-amino-3-[18F]fluoromethyl-cyclobutane-1-carboxylic acid (FMACBC), Potential PET ligands for tumor detection," *Journal of Medicinal Chemistry*, vol. 45, No. 11, 2002, pp. 2250-2259.
McCarthy et al., "Improved synthesis of anti-[18 F]FACBC: Improved preparation of labeling precursor and automated radiosynthesis," *Appl. Radiat. Isot.*, vol 58, No. 6, Jun. 2003, pp. 657-666.
Shoup et al., "Synthesis and evaluation of [18F]1-Amino-3-fluorocyclobutane-1-carboxylic acid to image brain tumors", *The Journal of Nuclear Medicine*, vol. 40, No. 2, pp. 331-338.

(Continued)

*Primary Examiner* — Michael G Hartley
*Assistant Examiner* — Sean R Donohue
(74) *Attorney, Agent, or Firm* — Fitch, Even, Tabin & Flannery LLP

(57) ABSTRACT

It is intended to provide a novel amino acid organic compound which can be used as a labeling precursor compound for radioactive halogen-labeled amino acid compounds including [$^{18}$F]FACBC, and which prevents methanol from remaining in the radioactive halogen-labeled amino acid compounds produced therefrom. The novel amino acid organic compound is a compound represented by the following formula:

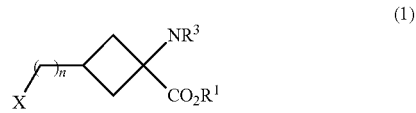

(1)

wherein n is an integer of 0 or of 1 to 4; $R^1$ is an ethyl, 1-propyl or isopropyl substituent; X is a halogen substituent or a group represented by —$OR^2$; $R^2$ is a straight-chain or branched-chain haloalkylsulfonic acid substituent with one to 10 carbon atoms, trialkylstannyl substituent with 3 to 12 carbon atoms, fluorosulfonic acid substituent or aromatic sulfonic acid substituent; and $R^3$ is a protective group.

2 Claims, 1 Drawing Sheet

(56) References Cited

OTHER PUBLICATIONS

Wang et al., "Syntheses of new conformationally constrained S-[2-[(1-iminoethyl)amino] ethyl] homocysteine derivatives as potential nitric oxide synthase inhibitors," *Heteroatom Chemistry*, vol. 13, No. 1, 2002, pp. 77-83.
PCT International Preliminary Report on Patentability in PCT/JP2006/323659, dated Jun. 3, 2008.
PCT Written Opinion of the International Search Authority in PCT/JP2006/323659.
Office Action dated Oct. 1, 2010, in Russian application 200812677.
Laurent Martarelli, et al., Synthesis of syn- and anti-1-Amino-3-[$^{18}$F]fluoromethyl-cyclobutane-1-carboxylic Acid (FMACBC), Potential PET Ligands for Tumor Detection, Journal of Medical Chemistry, Apr. 26, 2002, pp. 2250-2259, vol. 45, No. 11, American Chemical Society.
Communication from EPO in EP Appln. 06 833 463.0, dated Jul. 14, 2010.
Israel Office Action dated May 31, 2011, corresponding with Israel Patent Application 191184.
Office Action dated Mar. 1, 2011, in corresponding Australian application 2006319987.
JP Office Action corresponding with JP Patent Application 2007-547939.
Chinese Office Action issued against TW Patent Application 095143886.
Patent Examination Report No. 2 dated Jul. 5, 2012 issued against Australian Patent Application 2006319987.
Korean Office action dated Dec. 24, 2012, issued against corresponding Korean Application No. 10-2008-7012348, 4 pages, entire document.
Canadian Office action dated Dec. 31, 2012, issued against corresponding Canadian Application No. 2,629,227, 2 pages, entire document.
Molecular Imaging and Contrast Agent Database (MICAD) anti-1-Amino-3-[18F]fluorocyclobutane-1-carboxylic acid http://www.ncbi.nlm.nih.gov/books/NBK23315/.
Korean Office Action in Korean Application No. 10-2013-7022428, English language translation unavailable.

* cited by examiner

UNNATURAL AMINO ACID RADIOLABELING PRECURSOR

CROSS-REFERENCE TO RELATED APPLICATIONS

This is a U.S. National Phase of International Application PCT/JP2006/323659, filed Nov. 28, 2006, and claims the benefit of foreign priority under 35 U.S.C. §119 based on JP 2005-343653, filed Nov. 29, 2005, the entire disclosures of which applications are hereby incorporated herein by reference.

TECHNICAL FIELD

The present invention relates to a precursor compound which can be suitably used for production of radioactive halogen-labeled organic compounds or active ingredients for diagnostic agents used in positron emission tomography and single photon emission computed tomography.

BACKGROUND ART

Nuclear medicine examination represented by positron emission tomography (hereinafter referred to as PET) and single photon emission computed tomography (hereinafter referred to as SPECT), is effective in diagnosing a variety of diseases including heart disease and cancer. These techniques involve administering an agent labeled with a specific radio-isotope (hereinafter referred to as radiopharmaceutical) to a patient, followed by detecting γ-rays emitted directly or indirectly from the agent. Nuclear medicine examination is characteristic in that it has not only high specificity and sensitivity to diseases, but also an advantage of providing information on the functionality of lesions, compared to other examination techniques.

For example, [$^{18}$F]2-fluoro-2-deoxy-D-glucose (hereinafter referred to as "$^{18}$F-FDG"), one of radiopharmaceuticals used for PET examination, tends to be concentrated in area where glucose metabolism is enhanced, thereby making it possible to specifically detect tumors in which glucose metabolism is enhanced.

Nuclear medicine examination is performed by tracing a distribution of an administered radiopharmaceutical, and data obtained therefrom vary depending on nature of the radiopharmaceutical. Thus, different radiopharmaceuticals have been developed for different diseases, and some of them are put into clinical use. There have been developed, for example, various tumor diagnostic agents, bloodstream diagnostic agents and receptor mapping agents.

In recent years, a series of radioactive halogen-labeled amino acid compounds including [$^{18}$F]1-amino-3-fluorocyclobutanecarboxylic acid (hereinafter referred to as [$^{18}$F]FACBC) have been designed as novel radiopharmaceuticals, and their clinical application is under examination (Patent Document 1, and non-Patent Documents 1 and 2). [$^{18}$F]FACBC is considered to be effective as a diagnostic agent for highly proliferative tumors, because it has a property of being taken up specifically by amino acid transporter.

As processes for producing [$^{18}$F]FACBC, there are disclosed processes which include: providing 1-(N-(t-butoxycarbonyl)amino)-3-[((trifluoromethyl)sulfonyl)oxy]-cyclobutane-1-carboxylic acid methyl ester as a labeling precursor, substituting the triflate group at position 3 of the precursor with radioactive fluorine, and carrying out deprotection by subjecting the resulting compound to an acidic condition (Patent Document 1, and non-Patent Documents 1 and 2)

Patent Document 1: Japanese Patent Laid-open No. 2000-500442.

Non-Patent Document 1: Jonathan McConathy et al., "Improved synthesis of anti-[18F]FACBC: improved preparation of labeling precursor and automated radiosynthesis.", Applied Radiation and Isotopes, (Netherlands), 2003, 58, p. 657-666.

Non-Patent Document 2: Timothy M. Shoup et al., "Synthesis and Evaluation of [18F]1-Amino-3-fluorocyclobutane-1-carboxylic Acid to Image Brain Tumors.", The Journal of Nuclear Medicine, 1999, 40, p. 331-338.

DISCLOSURE OF THE INVENTION

Problems to be Solved by the Invention

However, investigations made by the present inventors have revealed that the processes for producing [$^{18}$F]FACBC disclosed up until now allow methanol to remain in the produced [$^{18}$F]FACBC as a residual solvent. Methanol is specified as a class 2 solvent in ICH guideline "Impurities: Guideline for Residual Solvents" and treated as a solvent whose level remaining in pharmaceuticals should be regulated.

The present invention has been made in light of the above described circumstances. Accordingly, an object of the present invention is to provide a novel amino acid organic compound which can be used as a labeling precursor compound for radioactive halogen-labeled amino acid compounds having a cyclobutane ring skeleton, including [$^{18}$F]FACBC, and which prevents methanol from remaining in the radioactive halogen-labeled amino acid compounds produced therefrom.

Means for Solving the Problems

As a result of investigation, the present inventors have found that when the ester bound to the carbon atom at position 1 of the cyclobutane ring is formed with an alkyl with 2 or 3 carbon atoms, it is possible to prevent methanol from remaining in the synthesized compound. Thus, the present invention has been accomplished.

The present invention provides a precursor compound for radioactive halogen-labeled organic compounds, which is represented by the following formula (1):

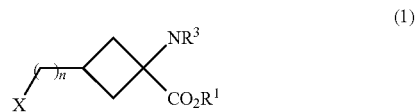

(1)

In the above formula (1), n is an integer of 0 or of 1 to 4 an appropriate value of which may vary depending on kinds of radioactive halogen-labeled amino acid compounds to be finally produced. For example, when the compound to be finally produced is a compound in which a halogen is directly bound to the position 3 of the cyclobutane ring (e.g. [$^{18}$F]FACBC), n is 0, while when the compound to be finally produced is a compound in which a halogen is bound to the position 3 of the cyclobutane ring via a methylene chain, such as [$^{18}$F]1-amino-3-fuluoromethylcyclobutanecarboxylic acid, n is 1.

In the above formula (1), $R^1$ represents an ethyl, 1-propyl or isopropyl substituent, and preferably an ethyl substituent.

In the above formula (1), X represents a halogen substituent or a group represented by —$OR^2$. $R^2$ is selected from the group consisting of straight-chain or branched-chain haloalkylsulfonic acid substituents with one to 10 carbon atoms, trialkylstannyl substituents with 3 to 12 carbon atoms, fluorosulfonic acid substituents and aromatic sulfonic acid substituents, and is preferably a substitutent selected from the group consisting of toluenesulfonic acid substituent, nitrobenzenesulfonic acid substituent, benzenesulfonic acid substituent, trifluoromethanesulfonic acid substituent, fluorosulfonic acid substituent, perfluoroalkylsulfonic acid substituent, trimethylstannyl substituent and triethylstannyl substituent. As a halogen substituent, a bromo or chloro substituent can be preferably used.

$R^3$ is selected from the group consisting of straight-chain or branched-chain alkyloxycarbonyl substituents with 2 to 7 carbon atoms, straight-chain or branched-chain alkenyloxycarbonyl substituents with 3 to 7 carbon atoms, benzyloxycarbonyl substituents having 7 to 12 carbon atoms which may be modified with a substitutent, alkyldithiooxycarbonyl substituents with 2 to 7 carbon atoms, straight-chain or branched-chain alkylamide substituents with one to 6 carbon atoms, straight-chain or branched-chain alkenylamide substituents with 2 to 6 carbon atoms, benzamide substituents with 6 to 11 carbon atoms which may be modified with a substituent, cyclic imide substituents with 4 to 10 carbon atoms, aromatic imine substituents with 6 to 11 carbon atoms which may have a substituent, straight-chain or branched-chain alkylamine substituents with one to 6 carbon atoms, straight-chain or branched-chain alkenylamine substituents with 2 to 6 carbon atoms, and benzylamine substituents with 6 to 11 carbon atoms which may have a substituent. Preferably $R^3$ is a substituent selected from the group consisting of t-butoxycarbonyl group, allyloxycarbonyl group, phthalimide group and N-benzylideneamine substituent, more preferably $R^3$ is t-butoxycarbonyl group or phthalimide group.

Effects of the Invention

The compound according to the present invention can be used as a labeling precursor compound for radioactive halogen-labeled amino acid compounds having a cyclobutane ring skeleton. By use of the compound according to the present invention as a labeling precursor, it has been made possible to prevent methanol from remaining in the produced radioactive halogen-labeled amino acid compounds.

BEST MODE FOR CARRYING OUT THE INVENTION

Next, a process for producing a compound of the present invention will be described taking, as an example, synthesis of syn-1-(N-(t-butoxycarbonyl)amino)-3-[((trifluoromethyl)sulfonyl)oxy]-cyclobutane-1-carboxylic acid ethyl ester shown in FIGS. 1 to 3.

First, a solution of syn-5-(3-benzyloxycyclobutane)hydantoin in a saturated barium hydroxide solution is refluxed, and sulfuric acid is added to the refluxed solution to adjust the pH of the same to about 7. The solution is then filtered and the filtrate is concentrated to allow syn-1-amino-3-benzyloxycyclobutane-1-carboxylic acid to precipitate as white crystals. The acid used for the pH adjustment may be an acid other than sulfuric acid, but it needs to be an acid that forms a water-insoluble inorganic salt with barium (FIG. 1, Step 1).

The syn-1-amino-3-benzyloxycyclobutane-1-carboxylic acid is fully dried to remove water and then dissolved in ethanol. A base and thionyl chloride are then added to the ethanol solution in this order, stirred at room temperature, and then heated under reflux at about 95° C. After the reaction has fully progressed, the solution is concentrated under reduced pressure to yield syn-1-amino-3-benzyloxycyclobutane-1-carboxylic acid ethyl ester as white crystals (FIG. 1, Step 2).

The base added to the reaction solution in the above step may be any base, as long as it can trap the hydrochloric acid produced during the reaction. Preferably triethylamine can be used. The amount of the base to be used is the same as or larger than that of thionyl chloride.

The amount of thionyl chloride needs to be the same as or larger than that of the reaction raw material, namely, syn-1-amino-3-benzyloxycyclobutane-1-carboxylic acid. If the amount of thionyl chloride is too small, it unfavorably occurs that ethyl esterification does not progress sufficiently. If the amount of thionyl chloride is too large, excess hydrochloric acid is produced, and thus a larger amount of base is unfavorably required. In preferred embodiments, the amount of thionyl chloride is equal to or smaller than 5 equivalents of syn-1-amino-3-benzyloxycyclobutane-1-carboxylic acid.

Then, syn-1-amino-3-benzyloxycyclobutane-1-carboxylic acid ethyl ester is added to a solution of a small amount of base in an alcohol solvent such as ethanol. The resultant suspension is stirred under cooling, and t-butyl dicarbonate is added to the suspension to allow them to react at room temperature (FIG. 1, Step 3). As the alcohol solvent, ethanol can be preferably used, though various kinds of alcohol can be used. The amount of the base is required to be sufficiently small relative to that of the alcohol, but if the amount is too small, the progress of the reaction becomes slow unfavorably. In preferred embodiments, a solution in which the ratio of alcohol to base is 9:1 is used. The amount of t-butyl dicarbonate needs to be one equivalent or more of syn-1-amino-3-benzyloxycyclobutane-1-carboxylic acid, and is preferably 1.5 equivalents of syn-1-amino-3-benzyloxycyclobutane-1-carboxylic acid.

This operation makes it possible to yield syn-1-(N-(t-butoxycarbonyl)amino)-3-benzyloxy-cyclobutane-1-carboxylic acid ethyl ester.

The syn-1-(N-(t-butoxycarbonyl)amino)-3-benzyloxycyclobutane-1-carboxylic acid ethyl ester synthesized as above is dissolved in an alcohol solvent such as ethanol or an acetate ester solvent such as ethyl acetate ester, and palladium-on-activated carbon (amount: 10 w/w % or more relative to the substrate) is added to the solution in an atmosphere of hydrogen to allow them to react under stirring at room temperature. The reaction solution is then filtered through Celite, and the filtrate is concentrated and purified to yield syn-1-(N-(t-butoxycarbonyl)amino)-3-hydroxy-cyclobutane-1-carboxylic acid ethyl ester (FIG. 2, Step 4).

The resultant syn-1-(N-(t-butoxycarbonyl)amino)-3-hydroxy-cyclobutane-1-carboxylic acid ethyl ester is dissolved in a base such as pyridine, followed by addition of trifluoromethanesulfonic anhydride. A target compound, syn-1-(N-(t-butoxycarbonyl)amino)-3-[((trifluoromethyl)sulfonyl)oxy]-cyclobutane-1-carboxylic acid ethyl ester is yielded by adding water, an organic solvent such as ether, and acid to the resultant solution and purifying the organic layer (FIG. 3, Step 5).

Compounds of the present invention other than the above described one can also be synthesized through the steps similar to those described above. For example, when a compound is synthesized in which a haloalkylsulfonic acid ester substituent other than the triflate substituent, an alkylsulfonic acid ester substituent or an aromatic sulfonic acid ester substituent is bound to the carbon atom at position 3 of the cyclobutane ring, the reaction in the step 5 can be carried out in the same manner as above, except that a different halogen sulfonyl or sulfonic anhydride is used instead of trifluoromethanesulfonic anhydride.

When a compound is synthesized in which a trialkylstannyl substituent is bound to the carbon atom at position 3 of the cyclobutane ring, an alcohol compound of syn-1-(N-(t-butoxycarbonyl)amino)-3-hydroxycyclobutane-1-carboxylic acid ethyl ester or the like is oxidized into a ketone or aldehyde compound, and the ketone or aldehyde compound is subjected to Wittig reaction using a phosphonium salt such as phosphonium iodomethylene to form a vinyl halide at position 3, followed by the reaction with a trialkyltin hydride. A compound in which a halogen is bound to the carbon atom at position 3 can be obtained by allowing the above described alcohol compound to react with a hydrogen halide or the like.

When a compound is synthesized in which an alkyloxycarbonyl substituent other than a t-butoxycarbonyl substituent, an alkenyloxycarbonyl substituent or a benzyloxycarbonyl substituent is bound to the amino group at position 1, the reaction in the above described step 3 can be performed using alkylchloroformates, alkenylchloroformates or benzylchloroformates respectively, instead of t-butyl dicarbonate. Similarly, when a compound is synthesized in which a cyclic imide substituent is bound to the amino group, various cyclic acid anhydrides such as phthalic anhydride can be used for the reaction with the amino group in the above described step 3. A compound in which an aromatic imine substituent is bound to the amino group can be synthesized by allowing benzaldehyde having a substituent to react with the amino group in the step 3. Compounds having other functional groups can also be synthesized using known methods in combination (Theodora W. Greene, "Protective groups in organic synthesis", 3$^{rd}$ edition, USA, Jon Wiley & Sons, Inc., 1999, pp. 531, 550-561, and 573-586).

When a 1-propylester form and isopropylester form are synthesized, 1-propanol and isopropanol may be used, respectively, as the alcohol for the reaction in the above step 2.

Next, as an example of use of the novel amino acid organic compounds according to the present invention, a method will be described in which anti-[$^{18}$F]FACBC is synthesized using the above synthesized syn-1-(N-(t-butoxycarbonyl)amino)-3-[((trifluoromethyl)sulfonyl)oxy]-cyclobutane-1-carboxylic acid ethyl ester.

The synthesis of anti-[$^{18}$F]FACBC is carried out in two steps: a step of adding radioactive fluorine to the precursor; and a step of deprotecting the compound to which radioactive fluoride has been added.

Radioactive fluorine can be obtained by a known method, for example, a method in which $H_2{}^{18}O$ enriched water is used as a target and exposed to proton bombardment. In this instance, radioactive fluorine exists in the $H_2{}^{18}O$ enriched water used as a target. The $H_2{}^{18}O$ enriched water containing radioactive fluorine is allowed to pass through, for example, an anion-exchange column so that the radioactive fluorine is adsorbed and collected on the column, thereby being separated from the $H_2{}^{18}O$ enriched water. Thereafter, a potassium carbonate solution is allowed to pass through the column to elute the radioactive fluorine, and the eluate is supplemented with a phase transfer catalyst and is evaporated to dryness, thereby activating the radioactive fluorine.

Then, the dried radioactive fluorine is dissolved in acetonitrile, and the syn-1-(N-(t-butoxycarbonyl)amino)-3-[((trifluoromethyl)sulfonyl)oxy]-cyclobutane-1-carboxylic acid ethyl ester, as a precursor, is added to the acetonitrile solution to allow them to react under heating. As a result, radioactive fluorine is added to the precursor, whereby anti-[$^{18}$F]1-(N-(t-butoxycarbonyl)amino)-3-fluorocyclobutane-1-carboxylic acid ethyl ester is synthesized.

The resultant anti-[$^{18}$F]1-(N-(t-butoxycarbonyl)amino)-3-fluorocyclobutane-1-carboxylic acid ethyl ester is deprotected to yield anti-[$^{18}$F]FACBC as a target compound. The deprotection can be performed, for example, by providing an acidic condition. The acidic condition can be provided by various methods, for example, a method in which an acid is added to a solution that contains anti-[$^{18}$F]1-(N-(t-butoxycarbonyl)amino)-3-fluorocyclobutane-1-carboxylic acid ethyl ester. The amount of the acid to be added need not be restricted as long as the amount can provide an acidic condition sufficient for the deprotection.

The other compounds of the present invention other than the above described compound can also be used as labeling precursors of radioactive halogen-labeled compounds in the manner similar to that described above.

For example, compounds in which a trialkylstannyl substituent is bound to the carbon atom at position 3 of the cyclobutane ring can be mixed and reacted with various radioactive halogens and oxidizers depending on the objective so as to yield radioactive halogen-labeled compounds. Compounds in which a halogen substituent is bound to the carbon atom at the position 3 can be labeled with a radioactive halogen using nucleophilic displacement reaction or isotopic exchange reaction. When labeling with a radioactive halogen is performed using nucleophilic displacement reaction, the following displacement reaction can be performed. For example, the halogen bound to the carbon atom at position 3 is iodine, the iodine can be displaced by fluorine, chlorine or bromine, when the halogen bound to the carbon atom at position 3 is bromine, the bromine can be displaced by chlorine or fluorine, and when the halogen bound to the carbon atom at position 3 is chlorine, the chlorine can be displaced by fluorine.

EXAMPLES

The present invention will be now described in further detail with reference to Examples; however, it should be understood that the details of the Examples are not intended to limit the present invention.

The analytical conditions under which gas chromatography was carried out in each Example and Comparative Example were as follows.

Apparatus: GC-1700AF/aoc (manufactured by Shimadzu Corporation)
Column: SPB-1 (manufactured by SUPELCO, 30 m×0.53 mm I.D., particle size of packing: 3 μm)
Column temperature: 40° C. (3.3 minutes)→90° C. (0.5 minutes) (temperature increase rate: 20° C./min)
Inlet temperature: 250° C.
Detector temperature: 220° C.
Carrier gas: helium
Split ratio: 1:10
Linear velocity: 30 cm/sec Example 1

Synthesis of syn-1-(N-(t-butoxycarbonyl)amino)-3-[((trifluoromethyl)sulfonyl)oxy]-cyclobutane-1-carboxylic acid ethyl ester Hydrolysis of syn-hydantoin (FIG. 1, Step 1)
Syn-5-(3-benzyloxycyclobutane)hydantoin was synthesized in accordance with the method described in a literature (Jonathan McConathy et al., Applied Radiation and Isotopes, 2003, 58, p. 657-666).

A solution of 72.8 g (corresponding to 0.418 mol) of 3-benzyloxycyclobutane-1-one in 2.86 L of ethanol was added dropwise to a solution prepared by dissolving 397 g (corresponding to 4.13 mol) of ammonium carbonate and 88.4 g (corresponding to 1.65 mol) of ammonium chloride in 2.86 L of water, and stirred at room temperature for 30 minutes. Then, 121.0 g (corresponding to 1.86 moles) of potassium cyanide was added to the mixture and stirred at 60° C. overnight. The reaction solution was concentrated, and the resultant yellow solid was washed with 1.06 L of water to remove salts. The solid was subjected to azeotropic distillation with 927 mL of methanol and purified by silica gel column chromatography (elution solvent: dichloromethane/methanol=98/2) to yield 55.3 g of syn-5-(3-benzyloxycyclobutane) hydantoin.

250 mL of saturated barium hydroxide solution was added to 6.15 g (corresponding to 25 mmol) of syn-5-(3-benzyloxycyclobutane)hydantoin and refluxed under heating in an oil bath at 114° C. for 24 hours or longer. Then, TLC analysis was performed using, as mobile solvents, two kinds of systems: chloroform/methanol=5/1 (Rf value of syn-hydantoin=around 0.6) and chloroform/methanol=95/1 (Rf value of syn-hydantoin=around 0.3), and the completion of the reaction was confirmed (by coloration with UV and phosphomolybdic acid).

After the completion of the reaction is confirmed, the reaction solution was cooled to room temperature, and about 24 mL of 1 mol/mL sulfuric acid was added to neutralize the reaction solution. After the neutralization, the reaction solution was further stirred at room temperature for 5 minutes, and the formed precipitate was removed by filtration. The filtrate was concentrated to yield 5.67 g of syn-1-amino-3-benzyloxycyclobutane-1-carboxylic acid as white crystals.

Ethyl esterification (FIG. 1, Step 2)

5.67 g of syn-1-amino-3-benzyloxycyclobutane-1-carboxylic acid, which had been fully dried to remove water, was dissolved in 200 mL of ethanol. To this solution, 9.5 mL (corresponding to 75 mmol) of triethylamine was added and cooled at −78° C. for 20 minutes, and then 4.6 mL (corresponding to 62.5 mmol) of thionyl chloride was added. The reaction solution was stirred at 0° C. for 1 hour and at room temperature for 1 hour, followed by heating under reflux in an oil bath at 95° C. overnight. The completion of the reaction was confirmed by TLC analysis using a mobile solvent of chloroform/methanol=95/1 (Rf value of the target compound=around 0.6) (confirmed by coloration with UV and phosphomolybdic acid). After the completion of the reaction is confirmed, the reaction solution was concentrated under reduced pressure to yield 7.64 g of syn-1-amino-3-benzyloxycyclobutane-1-carboxylic acid ethyl ester as white crystals.

Addition of Boc (FIG. 1, Step 3)

7.64 g of syn-1-amino-3-benzyloxycyclobutane-1-carboxylic acid ethyl ester was dissolved in 250 mL of a mixed solution of ethanol/triethylamine=9/1. After the solution was cooled in an ice bath for 15 minutes, 8.6 mL (corresponding to 37.5 mmol) of t-butyl dicarbonate was added to the solution and stirred at room temperature overnight. The completion of the reaction was confirmed by TLC analysis using a mobile solvent of hexane/ethyl acetate=1:1 (Rf value of the target compound=around 0.6) (confirmed by coloration with UV and molybdic acid). After the completion of the reaction was confirmed, the reaction solution was concentrated under reduced pressure to yield white crystals as a residue. To the residue, 150 mL of cooled ethyl acetate and 150 mL of 0.5 mol/L cooled hydrochloric acid were added, stirred in an ice bath for 5 minutes, and left to stand until separation occurred.

The organic layer was extracted and washed with 150 mL of water twice, with 150 mL of a saturated aqueous solution of sodium hydrogen carbonate, with 150 mL of water twice and with 150 mL of saturated saline solution twice in this order, dried with anhydrous sodium sulfate, and concentrated under reduced pressure to yield yellow oily matter. Separately, the water layer was extracted and washed with 150 mL of ethyl acetate twice, with 150 mL of water twice and with 150 mL of saturated saline solution in this order, dried with sodium sulfate anhydride, and concentrated under reduced pressure to recover a small amount of yellow oily matter. By these operations, 8.82 g of light yellow oily matter was obtained. The residue was purified by silica gel column chromatography (hexane/ethyl acetate=1/1) to yield 8.04 g (corresponding to 23 mmol) of syn-1-(N-(t-butoxycarbonyl)amino)-3-benzyloxy-cyclobutane-1-carboxylic acid ethyl ester as white crystals.

Debenzylation (FIG. 2, Step 4)

To 8.04 g (corresponding to 23 mmol) of syn-1-(N-(t-butoxycarbonyl)amino)-3-benzyloxy-cyclobutane-1-carboxylic acid ethyl ester, was added 150 mL of ethanol and then 960 mg of palladium-on-activated carbon (10% palladium) to perform replacement with hydrogen under stirring at room temperature overnight. After the reaction, palladium-on-activated carbon was removed by filtration using Celite, and the filtrate was concentrated under reduced pressure to yield 5.74 g of white crystals as a residue. The reaction was traced by TLC analysis using a mobile solvent of hexane/ethyl acetate=1/1 (Rf value of the target compound of reaction=around 0.2) (confirmed by coloration with UV and ninhydrin) to confirm the completion of the reaction. Then, the residue was purified by silica gel column chromatography (hexane/ethyl acetate=1/1, hexane/ethyl acetate=4/1) to yield 5.36 g (corresponding to 20.7 mmol) of syn-1-(N-(t-butoxycarbonyl)amino)-3-hydroxy-cyclobutane-1-carboxylic acid ethyl ester as white crystals.

Triflation (FIG. 3, Step 5)

2.07 g (8 mmol) of syn-1-(N-(t-butoxycarbonyl)amino)-3-hydroxy-cyclobutane-1-carboxylic acid ethyl ester was dissolved in 26 mL of pyridine and stirred in an ice bath for 20 minutes. Then, 2.0 mL (corresponding to 12 mmol) of trifluoromethanesulfonic anhydride was added and stirred for 30 minutes. The reaction was traced by TLC analysis using a mobile solvent of hexane/diethyl ether=1:1 (Rf value of target compound of reaction=around 0.6) (confirmed by coloration with ninhydrin) to confirm the completion of the reaction. After confirming the completion of the reaction, 100 mL of water and 100 mL of ether were added to the reaction solution, and extraction and washing was performed with 100 mL of 1 mol/L hydrochloric acid twice, with 100 mL of water twice and with 100 mL of saturated saline solution twice in this order. After drying with sodium sulfate anhydride, concentration under reduced pressure was performed to yield 2.78 g of light yellow crystals. The reaction mixture was purified by silica gel chromatography (hexane/diethyl ether=3/1) to yield white crystals, and the resultant white crystals were again recrystallized using pentane/diethyl ether to yield 1.84 g (corresponding to 4.7 mmol) of syn-1-(N-(t-butoxycarbonyl)amino)-3-[((trifluoromethyl)sulfonyl)oxy]-cyclobutane-1-carboxylic acid ethyl ester.

The NMR measurement results (internal standard: tetramethylsilane) of the obtained syn-1-(N-(t-butoxycarbonyl)amino)-3-[((trifluoromethyl)sulfonyl)oxy]-cyclobutane-1-carboxylic acid ethyl ester were as follows.

NMR apparatus used: JNM-ECP-500 (manufactured by JEOL, Ltd.)

$^1$H-NMR (solvent: CDCl$_3$, resonance frequency: 500 MHz): δ5.41-5.35 (m, 1H), 5.32 (b, 1H), 4.26 (q, 2H, J=7 Hz), 3.10-3.02 (m, b, 4H), 1.45 (s, 9H), 1.31 (t, 3H, J=7.0 Hz)

$^{13}$C-NMR (solvent: CDCl$_3$, resonance frequency: 125 MHz): δ172.60, 154.46, 118.48, 75.88, 51.97, 40.87, 28.29, 14.11

Comparative Example 1

Anti-[$^{18}$F]FACBC was synthesized using syn-1-(N-(t-butoxycarbonyl)amino)-3-[((trifluoromethyl)sulfonyl)oxy]-cyclobutane-1-carboxylic acid methyl ester as a labeling precursor, and the measurement was made of the residual solvent in the synthesized anti-[$^{18}$F]FACBC.

Syn-1-(N-(t-butoxycarbonyl)amino)-3-[((trifluoromethyl)sulfonyl)oxy]-cyclobutane-1-carboxylic acid methyl ester was synthesized in accordance with a method described in a literature (Jonathan McConathy et al., Applied Radiation and Isotopes, 2003, 58, p. 657-666).

[$^{18}$F]fluoride ion-containing H$_2$$^{18}$O (radioactivity: 3.27 GBq, a corrected value at the time of starting synthesis) was allowed to pass through an anion-exchange column to adsorb and collect [$^{18}$F]fluoride ion on the column. Then, a mixture of an aqueous solution of potassium carbonate (133 mmol/L, 0.3 mL) and a solution of 40 mg of Kryptfix 222 (under trade name, manufactured by Merck & Co., Inc.) in 1.5 mL of acetonitrile was allowed to pass through the same column to elute [$^{18}$F]fluoride ion.

The eluate was heated to 110° C. to evaporate water, and was subjected to azeotropic distillation with addition of acetonitrile (0.5 mL×2), followed by evaporation to dryness. To the dried [$^{18}$F]fluoride, a solution of 30 mg of 1-(N-(t-butoxycarbonyl)amino)-3-[((trifluoromethyl)sulfonyl)oxy]-cyclobutane-1-carboxylic acid methyl ester in 1 mL of acetonitrile was added and heated at 85° C. for 3 minutes. Then, 4 mL of diethyl ether was added to the solution and further 3 mL of the same was added twice, and the mixture was allowed to pass through Sep-PakSilica (under trade name, manufactured by Japan Waters) to yield a solution of a [$^{18}$F]fluorine-labeled compound in acetonitrile/diethyl ether.

To the obtained solution of the [$^{18}$F]fluorine-labeled compound in acetonitrile/diethyl ether, 1.5 mL of 4 mol/L hydrochloric acid was added and heated at 120° C. for 15 minutes to perform deprotection to yield anti-[$^{18}$F]FACBC. The obtained anti-[$^{18}$F]FACBC was subjected to gas chromatography under the above described conditions to quantitatively determine methanol and ethanol. As shown in Table 1, methanol was detected at concentrations of 17.4±0.6 ppm.

TABLE 1

Quantitative analyses of methanol and ethanol

| Solvent | | Content (ppm) | Average (ppm) | Standard deviation |
|---|---|---|---|---|
| Methanol | 1 | 18.0 | 17.4 | 0.6 |
|  | 2 | 17.1 |  |  |
|  | 3 | 17.0 |  |  |
| Ethanol | 1 | not detected |  |  |
|  | 2 | not detected |  |  |
|  | 3 | not detected |  |  |

Example 2

[$^{18}$F]fluoride ion-containing H$_2$$^{18}$O (radioactivity: 36.63 GBq, a corrected value at the time of starting synthesis) was allowed to pass through an anion-exchange column to adsorb and collect [$^{18}$F]fluoride ion on the column. Then, a mixed solution of an aqueous solution of potassium carbonate (133 mmol/L, 0.3 mL) and a solution of 40 mg of Kryptfix 222 (under trade name, manufactured by Merck & Co., Inc.) in 1.5 mL of acetonitrile was allowed to pass through the same column to elute [$^{18}$F]fluoride ion.

The eluate was heated to 110° C. to evaporate water, and was subjected to azeotropic distillation with addition of acetonitrile (0.5 mL×2), followed by evaporation to dryness. To the dried [$^{18}$F]fluoride, a solution of 32 mg of syn-1-(N-(t-butoxycarbonyl)amino)-3-[((trifluoromethyl)sulfonyl)oxy]-cyclobutane-1-carboxylic acid ethyl ester obtained in Example 1 in 1 mL of acetonitrile was added and heated at 85° C. for 3 minutes. Then, 4 mL of diethyl ether was added to the solution and further 3 mL of the same was added twice, and the mixture was allowed to pass through Sep-PakSilica (under trade name, manufactured by Japan Waters) to yield a solution of a [$^{18}$F]fluorine-labeled compound in acetonitrile/diethyl ether.

To the obtained solution of the [$^{18}$F]fluorine-labeled compound in acetonitrile/diethyl ether, 1.5 mL of 4 mol/L hydrochloric acid was added and heated at 120° C. for 15 minutes to perform deprotection to yield anti-[$^{18}$F]FACBC. The obtained anti-[$^{18}$F]FACBC was subjected to gas chromatography to quantitatively determine methanol and ethanol. As shown in Table 2, no methanol was detected, while ethanol was detected at concentrations of 24.1±0.8 ppm.

The results so far confirmed that the use of a compound according to the present invention as a labeling precursor makes it possible to prevent methanol from remaining in the synthesized anti-[$^{18}$F]FACBC.

TABLE 2

Analyses of methanol and ethanol

| Solvent | | Content (ppm) | Average (ppm) | Standard deviation |
|---|---|---|---|---|
| Methanol | 1 | not detected |  |  |
|  | 2 | not detected |  |  |
|  | 3 | not detected |  |  |
| Ethanol | 1 | 24.5 | 24.1 | 0.8 |
|  | 2 | 23.1 |  |  |
|  | 3 | 24.6 |  |  |

Industrial Applicability

The compound of the present invention provides radioactive halogen-labeled organic compounds which are used as radiopharmaceuticals in nuclear medicine examination using PET or SPECT, and is useful in the field of radiopharmaceuticals.

Figure 1:
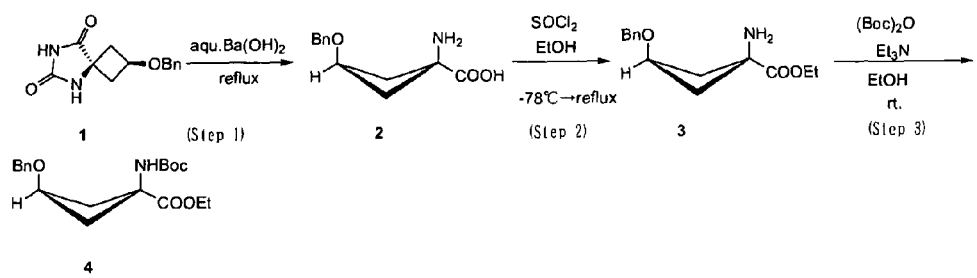
FIG. 1 shows a scheme of synthesis of syn-1-(N-(t-butoxycarbonyl)amino)-3-benzyloxy-cyclobutane-1-carboxylic acid ethyl ester.
Figure 2:
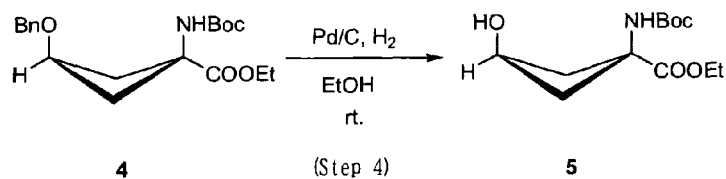
FIG. 2 shows a scheme of synthesis of syn-1-(N-(t-butoxycarbonyl)amino)-3-hydroxy-cyclobutane-1-carboxylic acid ethyl ester.
Figure 3:
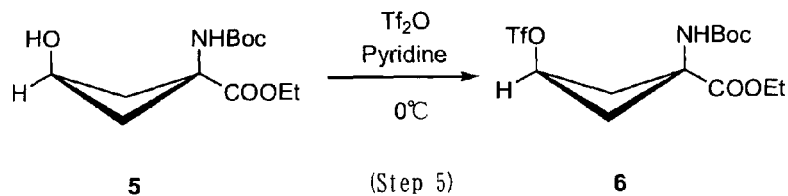
FIG. 3 shows a scheme of synthesis of syn-1-(N-(t-butoxycarbonyl)amino)-3-[((trifluoromethyl)sulfonyl)oxy]-cyclobutane-1-carboxylic acid ester.

The invention claimed is:

1. A precursor compound for a radioactive halogen-labeled organic compound, which is represented by the following formula (1):

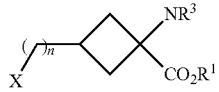
(1)

wherein
the radioactive halogen-labeled organic compound is 1-amino-3-[$^{18}$F]fluorocyclobutanecarboxylic acid;
n is 0;
$R^1$ is an ethyl substituent;
X is a trifluoromethanesulfonic acid substituent;
$R^3$ is a t-butoxycarbonyl group; and
the precursor compound substantially does not give methanol in the production of 1-amino-3-[$^{18}$F]fluorocyclobutanecarboxylic acid from the precursor compound.

2. A precursor compound for a radioactive halogen-labeled organic compound, which is represented by the following formula (2):

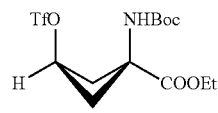
(2)

wherein
the radioactive halogen-labeled organic compound is anti-1-amino-3-[$^{18}$F]fluorocyclobutanecarboxylic acid;
Et is an ethyl substituent;
TfO is a trifluoromethanesulfonic acid substituent;
Boc is a t-butoxycarbonyl group; and
the precursor compound substantially does not give methanol in the production of anti-1-amino-3-[$^{18}$F]fluorocyclobutanecarboxylic acid from the precursor compound.

* * * * *

UNITED STATES PATENT AND TRADEMARK OFFICE
CERTIFICATE OF CORRECTION

PATENT NO. : 8,758,724 B2
APPLICATION NO. : 12/085679
DATED : June 24, 2014
INVENTOR(S) : Osamu Ito et al.

It is certified that error appears in the above-identified patent and that said Letters Patent is hereby corrected as shown below:

In the Claims

Column 11, lines 7-10, Claim 1, correct the formula (1) to read as follows:

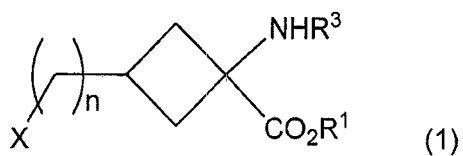

Signed and Sealed this
Fifth Day of July, 2016

Michelle K. Lee
*Director of the United States Patent and Trademark Office*